US009867901B2

(12) United States Patent
Feng et al.

(10) Patent No.: US 9,867,901 B2
(45) Date of Patent: *Jan. 16, 2018

(54) METHOD FOR MAKING NERVE GRAFT

(75) Inventors: Chen Feng, Beijing (CN); Li Fan, Beijing (CN); Wen-Mei Zhao, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 33 days.

This patent is subject to a terminal disclaimer.

(21) Appl. No.: 12/981,572

(22) Filed: Dec. 30, 2010

(65) Prior Publication Data
US 2012/0149112 A1    Jun. 14, 2012

(30) Foreign Application Priority Data

Dec. 11, 2010    (CN) .............................. 201010583250

(51) Int. Cl.
C12N 5/079    (2010.01)
A61L 27/08    (2006.01)
A61L 27/30    (2006.01)
A61L 27/34    (2006.01)
A61L 27/38    (2006.01)

(52) U.S. Cl.
CPC ............ *A61L 27/08* (2013.01); *A61L 27/303* (2013.01); *A61L 27/34* (2013.01); *A61L 27/383* (2013.01); *A61L 27/3878* (2013.01); *A61L 2400/12* (2013.01); *A61L 2420/04* (2013.01); *A61L 2430/32* (2013.01)

(58) Field of Classification Search
CPC ........ A61L 27/08; A61L 27/303; A61L 27/34; A61L 2430/32; A61L 27/3878; A61L 2400/12; A61L 2420/04; A61L 27/383
See application file for complete search history.

(56) References Cited

U.S. PATENT DOCUMENTS

2006/0204738 A1* 9/2006 Dubrow et al. ............ 428/292.1
2008/0089828 A1* 4/2008 Soga et al. ................. 423/447.2
2009/0198117 A1* 8/2009 Cooper ............... A61B 5/14532
                                                          600/347
2010/0144004 A1* 6/2010 Zhong et al. ............... 435/173.8

FOREIGN PATENT DOCUMENTS

CN    101643702 A    2/2010
CN    101693125 A    4/2010
TW    200639249      11/2006
TW    201006923 A    2/2010

OTHER PUBLICATIONS

Matsumoto et al., J Biosci and Bioeng, 103(3):216-220, 2007.*

Cranford et al., Journal of Mechanics and Physics of Solids, 58:409-427, Nov. 2009.*
Bunting et al., Journal of Hand Surgery, 30B:3:242-247, 2005.*
Jia et al., Materials Sci and Engineering—A, 528:1553-1557, published online Nov. 3, 2010.*
Boccaccini, et al. Adv Func Mater., 17:2815-2822, 2007.*
Zhang et al. Nano Letters 8(8):2564-2569, published Jul. 9, 2008.*
Zhang X. et al., "Guided neurite growth on patterned carbon nanotubes", Sensors and Actuators B, 2005, vol. 106, pp. 843-850.*
Galvan-Garcia P. et al., "Robust cell migration and neuronal growth on pristine carbon nanotube sheets and yarns", J. Biomater. Sci. Polymer Edn., 2007, vol. 18, No. 10, pp. 1245-1261.*
Wang K. et al., "Neural Stimulation with a Carbon Nanotube Microelectrode Array", Nano Letters, 2006, vol. 6, No. 9, pp. 2043-2048.*
Sunden E.O., "Carbon Nanotube Synthesis for Microsystems Applications", A Masters Thesis in Mechanical Engineering presented to the Georgia Institute of Technology, Aug. 2006, total pp. 127.*
F,Yang.et al."Electrospinning of nano/micro scale poly(L-lactic acid) aligned fibers and their potential in neural tissue engineering"; Biomaterials; vol. 26, 2005, pp. 2603-2610.
Nguyen-Vu et al. "Vertically Aligned Carbon Nanofiber Architecture as a Multifunctional 3-D Neural Electrical Interface" IEEE Transactions on Biomedical Engineering, vol. 54, No. 6, June 2007. pp. 1121-1128.
Weijie Huang et al. "Attaching Proteins to Carbon Nanotubes via Diimide-Activated Amidation" NANO Letters, 2002, vol. 2, No. 4 pp. 311-314.
Zhang Jinchao et al. "Application of Nanomaterials in Tissue Engineering" Progress in Chemistry, vol. 22 No. 11, Nov. 2010, pp. 2232-2237.
Kotaro Matsumoto et al. "Neurite outgrowths of neurons with neurotrophin-caoted carbon nanotubes" J. Biosci. Bioeng., 103, 2007, pp. 216-220.
Xuan Zhanga et al. "Guided neurite growth on patterned carbon nanotubes" Sensors and Actuators B, vol. 106, 2005 pp. 843-850.
Sensenbrenner M, et al.;"Neuronal cells from chick embryo cerebral hemisp heres cultivated on polylysine-coated surfaces"; Developmental Neuroscience, vol. 1, No. 2, p. 90-101, 1978.

(Continued)

*Primary Examiner* — Satyendra K Singh
(74) *Attorney, Agent, or Firm* — Steven Reiss

(57) ABSTRACT

A method for making a nerve graft includes the following steps. A culture layer including a lyophobic substrate, a carbon nanotube film structure, and a protein layer is provided. The carbon nanotube film structure is sandwiched between the lyophobic substrate and the protein layer. A number of nerve cells are seeded on a surface of the protein layer away from the lyophobic substrate. The nerve cells are cultured until a number of neurites branch from the nerve cells and are connected between the nerve cells.

12 Claims, 12 Drawing Sheets

(56) References Cited

OTHER PUBLICATIONS

Tamir Gabay et al., "Engineered selforganization of neural networks using carbon nanotube clusters", Physica A 350; 2005; pp. 611-621.
Stephanie K Seidlits et al., "Nanostructured scaffolds for neural applications"; Nanomedicine; 2008; vol. 3 Issue 2, pp. 183-199.
R Sorkin, et al., "Compact self-wiring in cultured neural networks"; Journal of Neural Engineering; Apr. 11, 2006; vol. 3 Issue:2 pp. 95-101.

* cited by examiner

METHOD FOR MAKING NERVE GRAFT

CROSS-REFERENCES TO RELATED APPLICATIONS

This application claims all benefits accruing under 35 U.S.C. §119 from China Patent Application No. 201010583205.9, filed on Dec. 11, 2010, in the China Intellectual Property Office, the disclosure of which is incorporated herein by reference. This application is related to commonly-assigned applications entitled, U.S. Ser. No. 12/981,573 "NERVE GRAFT," filed Dec. 30, 2010, U.S. Ser. No. 12/981,581 "METHOD FOR MAKING NERVE GRAFT," filed Dec. 30, 2010 and U.S. Ser. No. 12/981,584 "NERVE GRAFT," filed Dec. 30, 2010.

BACKGROUND

1. Technical Field

The present disclosure relates to a method for making a biological graft, especially to a method for making a nerve graft.

2. Description of Related Art

A nervous system is a complex cellular communication network that is mainly composed of neurons and glial cells (neuroglial cells). Glial cells occupy spaces between neurons and modulate neurons' functions. The neuron sense features of both external and internal environments and transmit this information to the brain for processing and storage. For example, the neurons receive the diverse types of stimuli from the environment (e.g. light, touch, sound) and convert into electric signals, which are then converted into chemical signals to be passed on to other cells.

Neurons exist in a number of different shapes and sizes, and can be classified by their morphology and function. The basic morphology of a neuron consists of a cell body and neurites projecting/branching from the cell body towards other neurons. The neurites also can be defined into two types by their functions. One is a dendrite, which branches around the cell body and receive signals from other neurons to cell body. The other is an axon, which branches from the cell body and grows continually without tapering. The axon conducts the signals away from the neuron's cell body. The end of the axon has branching terminals that release neurotransmitter substances acting as chemical signals into a gap between the branching terminals and the dendrites of other neurons. Thus, the information or signal is propagated.

Once injury to the nervous system occurs, neuron damage will lead to neurite degeneration and retraction. If the damage is severe, breaks in neurites of the neuron are presented. Consequentially, the signal transmission will be affected and the cellular communication with specific neurons will cease. Generally, damage on the neurites will reverse by introducing nerve pipes consisting of degradable biological material to the nervous system to reconnect with the opposite terminals in broken neurites. The neurites grow along the nerve pipes until the neurites are combined together. Thus, the neuron damage is reversed.

However, if a distance between the broken neurites is long, a growing time of the neurites can be long, thus a long recovery time for reversing the neuron damage is required.

What is needed, therefore, is to provide a method for making a nerve graft, to overcome the above-described shortcomings.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

Figure 1:
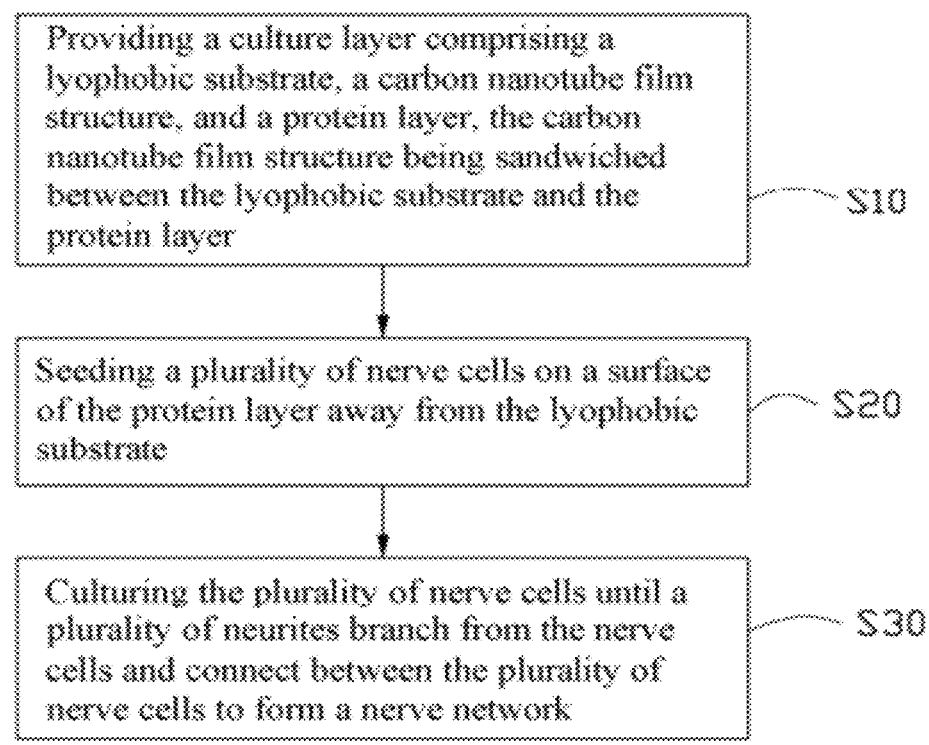
FIG. 1 shows a schematic structural view of a flow chart of one embodiment of a method for making a nerve graft.

The disclosure is illustrated by way of example and not by way of limitation in the figures of the accompanying drawings. It should be noted that references to "an" or "one" embodiment in this disclosure are not necessarily to the same embodiment, and such references mean at least one.

A method for making a nerve graft of one embodiment can include the following steps:

S10, providing a culture layer comprising a lyophobic substrate, a carbon nanotube film structure, and a protein layer, the carbon nanotube film structure being sandwiched between the lyophobic substrate and the protein layer;

S20, seeding a plurality of nerve cells on a surface of the protein layer away from the lyophobic substrate; and S30, culturing the plurality of nerve cells until a plurality of neurites branch from the nerve cells and connect between the plurality of nerve cells to form a nerve network.

In step S10, the lyophobic substrate is configured to load the carbon nanotube film structure. The lyophobic substrate can improve a mechanical strength of the culture layer, and prevent the carbon nanotube film structure from being damaged by an external force. The lyophobic substrate has a lyophobic property, thus a biological element such as the nerve cell, cannot be cultured in a growth surrounding supplied by the lyophobic substrate. The lyophobic substrate is innoxious to a biological element such as the nerve cell, thus the lyophobic substrate can be suitable for loading the nerve network and being transplanted into a biological body. In one embodiment, the lyophobic substrate is a silica gel substrate or a substrate coated with silica gel. The lyophobic substrate can also be a soft substrate, as such, a shape of the lyophobic substrate can be formed as desired. The shape of the lyophobic substrate can correspond to a shape of the carbon nanotube film structure.

The carbon nanotube film structure can be capable of forming a free-standing structure. The term "free-standing structure" can be defined as a structure that does not have to be supported by a substrate. For example, a free-standing structure can sustain the weight of itself if the free-standing structure is hoisted by a portion thereof without any significant damage to its structural integrity. The carbon nanotubes distributed in the carbon nanotube film structure defines a plurality of gaps therebetween. An average gap can be in a range from about 0.2 nanometers to about 9 nanometers. The carbon nanotubes can have a significant van der Waals attractive force therebetween. The free-standing structure of the carbon nanotube film structure is realized by the carbon nanotubes joined by van der Waals attractive force. As such, if the carbon nanotube film structure is placed between two separate supporters, a portion of the carbon nanotube film structure not in contact with the two supporters would be suspended between the two supporters and yet maintain film structural integrity.

The carbon nanotubes in the carbon nanotube film structure can be orderly or disorderly arranged. The term 'disordered carbon nanotube film structure' includes, but is not limited to, a structure where the carbon nanotubes are arranged along many different directions such that the number of carbon nanotubes arranged along each different direction can be almost the same (e.g. uniformly disordered), and/or entangled with each other. 'Ordered carbon nanotube film structure' includes, but is not limited to, a structure where the carbon nanotubes are arranged in a consistently systematic manner, e.g., the carbon nanotubes are arranged approximately along a same direction and or have two or more sections within each of which the carbon nanotubes are arranged approximately along a same direction (different sections can have different directions). The carbon nanotubes in the carbon nanotube film structure can be single-walled, double-walled, and/or multi-walled carbon nanotubes.

Macroscopically, the carbon nanotube film structure may have a substantially planar structure. The planar carbon nanotube film structure can have a thickness of about 0.5 nanometers to about 100 microns. The carbon nanotube film structure includes a plurality of carbon nanotubes and defines a plurality of micropores having a size of about 1 nanometer to about 500 nanometers. The carbon nanotube film structure includes at least one carbon nanotube film, the at least one carbon nanotube film including a plurality of carbon nanotubes substantially parallel to a surface of the corresponding carbon nanotube film. The carbon nanotube film structure can includes at least one carbon nanotube film. If the carbon nanotube film structure includes a plurality of carbon nanotube films stacked together. Adjacent carbon nanotube films can only be adhered by van der Waals attractive force therebetween.

Figure 2:
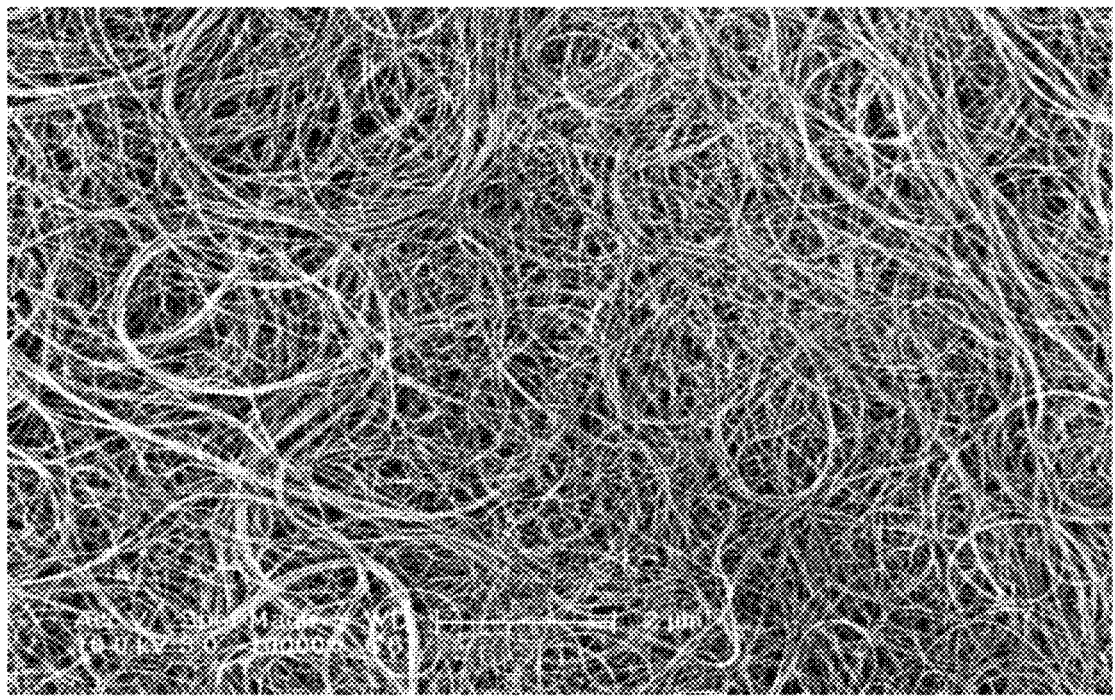
FIG. 2 shows a Scanning Electron Microscope (SEM) image of a flocculated carbon nanotube film.

The carbon nanotube film structure can include a flocculated carbon nanotube film as shown in FIG. 2. The flocculated carbon nanotube film can include a plurality of long, curved, disordered carbon nanotubes entangled with each other and can form a free-standing structure. Further, the flocculated carbon nanotube film can be isotropic. The carbon nanotubes can be substantially uniformly dispersed in the flocculated carbon nanotube film. The adjacent carbon nanotubes are acted upon by the van der Waals attractive force therebetween, thereby forming an entangled structure with micropores defined therein. Alternatively, the flocculated carbon nanotube film is porous. Sizes of the micropores can be about 1 nanometer to about 500 nanometers. Further, due to the carbon nanotubes in the carbon nanotube film structure being entangled with each other, the carbon nanotube film structure employing the flocculated carbon nanotube film has excellent durability and can be fashioned into desired shapes with a low risk to the integrity of the carbon nanotube film structure. The flocculated carbon nanotube film, in some embodiments, will not require the use of a structural support due to the carbon nanotubes being entangled and adhered together by van der Waals attractive force therebetween. The flocculated carbon nanotube film can define a plurality of micropores having a diameter of about 1 nanometer to about 500 nanometers.

Figure 3:
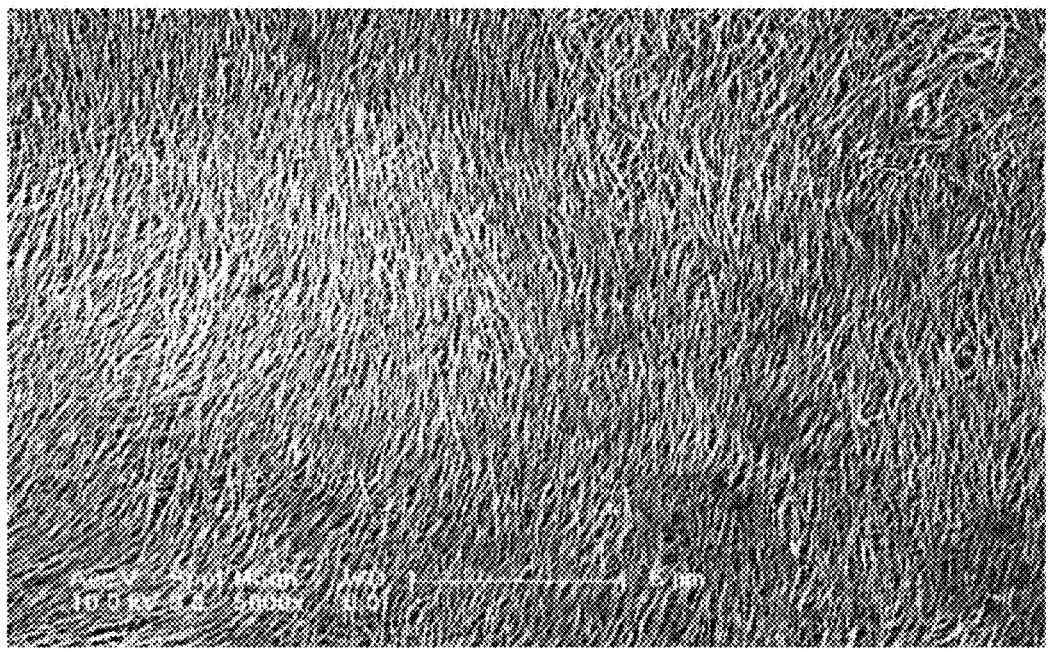
FIG. 3 shows an SEM image of a pressed carbon nanotube film.

The carbon nanotube film structure can include a pressed carbon nanotube film. The carbon nanotubes in the pressed carbon nanotube film can be arranged along a same direction or arranged along different directions. The carbon nanotubes in the pressed carbon nanotube film can rest upon each other. The adjacent carbon nanotubes are combined and attracted to each other by van der Waals attractive force, and can form a free-standing structure. An angle between a primary alignment direction of the carbon nanotubes and a surface of the pressed carbon nanotube film can be in a range from approximately 0 degrees to approximately 15 degrees. The pressed carbon nanotube film can be formed by pressing a carbon nanotube array. The angle is closely related to pressure applied to the carbon nanotube array. The greater the pressure, the smaller the angle. The carbon nanotubes in the carbon nanotube film are substantially parallel to the surface of the carbon nanotube film if the angle is about 0 degrees. A length and a width of the carbon nanotube film can be set as desired. The pressed carbon nanotube film can include a plurality of carbon nanotubes substantially aligned along one or more directions. The pressed carbon nanotube film can be obtained by pressing the carbon nanotube array with a pressure head. Alternatively, the shape of the pressure head and the pressing direction can determine the direction of the carbon nanotubes arranged therein. Specifically, in one embodiment, a planar pressure head is used to press the carbon nanotube array along the direction substantially perpendicular to a substrate. A plurality of carbon nanotubes pressed by the planar pressure head may be sloped in many directions. In another embodiment, as shown in FIG. 3, if a roller-shaped pressure head is used to press the carbon nanotube array along a certain direction, the pressed carbon nanotube film having a plurality of carbon nanotubes substantially aligned along the certain direction can be obtained. In another embodiment, if the roller-shaped pressure head is used to press the carbon nanotube array along different directions, the pressed carbon nanotube film having a plurality of carbon nanotubes substantially aligned along different directions can be obtained. The pressed carbon nanotube film can define a plurality of micropores having a diameter of about 1 nanometer to about 500 nanometers.

Figure 4:
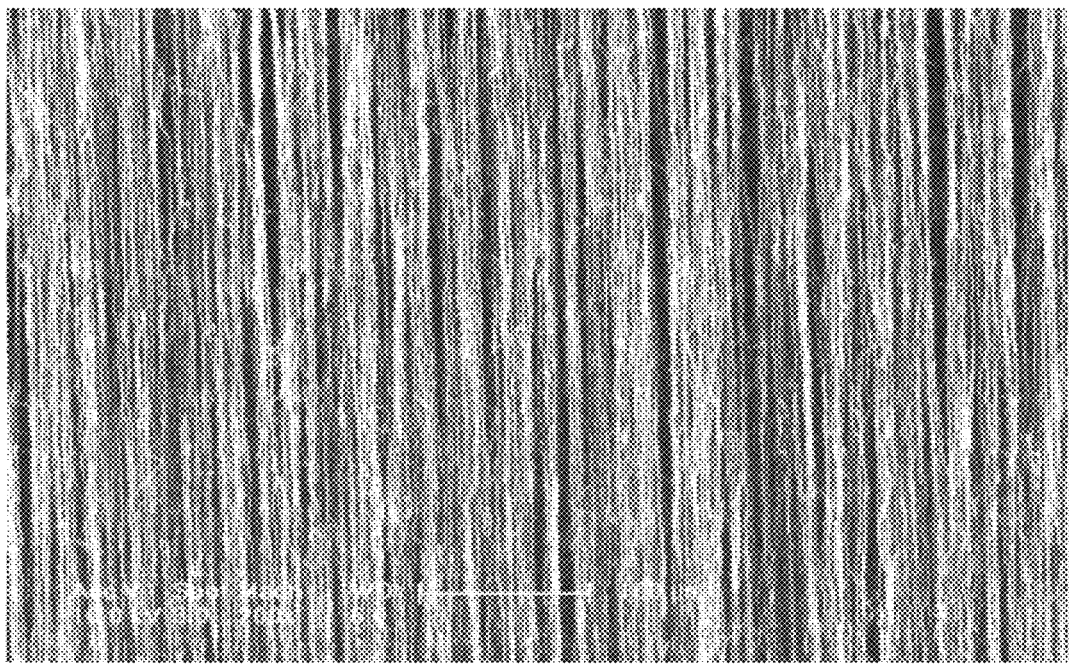
FIG. 4 shows an SEM image of a drawn carbon nanotube film.

In some embodiments, the carbon nanotube film structure includes at least one drawn carbon nanotube film as shown in FIG. 4. The drawn carbon nanotube film can have a thickness of about 0.5 nanometers to about 100 microns. The drawn carbon nanotube film includes a plurality of carbon nanotubes that can be arranged substantially parallel to a surface of the drawn carbon nanotube film. A plurality of micropores having a size of about 1 nanometer to about 500 nanometers can be defined by the carbon nanotubes. A large number of the carbon nanotubes in the drawn carbon nanotube film can be oriented along a preferred orientation, meaning that a large number of the carbon nanotubes in the drawn carbon nanotube film are arranged substantially along the same direction. An end of one carbon nanotube is joined to another end of an adjacent carbon nanotube arranged substantially along the same direction, by van der Waals attractive force. More specifically, the drawn carbon nanotube film includes a plurality of successively oriented carbon nanotube segments joined end-to-end by van der Waals attractive force therebetween. Each carbon nanotube segment includes a plurality of carbon nanotubes substantially parallel to each other and joined by van der Waals attractive force therebetween. The carbon nanotube segments can vary in width, thickness, uniformity, and shape. A small number of the carbon nanotubes are randomly arranged in the drawn carbon nanotube film and has a small if not negligible effect on the larger number of the carbon nanotubes in the drawn carbon nanotube film arranged substantially along the same direction.

Understandably, some variation can occur in the orientation of the carbon nanotubes in the drawn carbon nanotube film as can be seen in FIG. 3. Microscopically, the carbon nanotubes oriented substantially along the same direction may not be perfectly aligned in a straight line, and some curve portions may exist. Furthermore, it can be understood that some carbon nanotubes are located substantially side by side and oriented along the same direction and in contact with each other.

The carbon nanotube film structure can include a plurality of stacked drawn carbon nanotube films. Adjacent drawn carbon nanotube films can be adhered by only the van der Waals attractive force therebetween. An angle can exist between the carbon nanotubes in adjacent drawn carbon nanotube films. The angle between the aligned directions of the adjacent drawn carbon nanotube films can range from 0 degrees to about 90 degrees. In one embodiment, the angle between the aligned directions of the adjacent drawn carbon nanotube films is substantially 90 degrees. Simultaneously, aligned directions of adjacent drawn carbon nanotube films can be substantially perpendicular to each other, thus a plurality of micropores and nodes can be defined by the carbon nanotube film structure.

The protein layer is positioned on the carbon nanotube film structure to form a hydrophilic and bio-compatible surrounding on the carbon nanotube film structure. In one embodiment, the protein layer is located on a surface of the carbon nanotube film structure away from the lyophobic substrate. The protein layer can be fibrous protein, enzyme protein, or blood serum. The protein layer can include soluble protein and insoluble protein. The term "soluble protein" can be defined as a protein capable of interacting with water. In one embodiment, there can be a plurality of hydrophilic amino acids disposed on the outer surface of the soluble protein to interact with water. In one embodiment, the protein layer includes blood serum of a mammal, such as a cow, a pig, or human. The blood serum cannot only define a hydrophilic and bio-compatible surrounding on the carbon nanotube film structure, but can also supply a cell growth factor for the nerve cells or the nerve network.

Means for fabricating the culture layer is not limited, provided the protein layer and the carbon nanotube film structure are mixed together. For example, the culture layer can be fabricated by soaking the carbon nanotube film structure located on the lyophobic substrate with a protein solution. A volume ratio between the protein and the protein solution is from about 50% to about 100%. Thus, the protein solvent can be a pure protein, or a solution including the protein and a biological media dissolving the protein.

If the carbon nanotube film structure is soaked by the protein solution, the protein solution can infiltrate into the micropores defined in the carbon nanotube film structure. Thus, the carbon nanotubes of the carbon nanotube film structure can be soaked by the protein solution. Therefore, the carbon nanotubes can be wrapped by the protein layer. Alternatively, the protein layer can wrap all of the carbon nanotubes or part of the carbon nanotubes, provided the protein layer can cover at least part of the surface of the carbon nanotube film structure away from the lyophobic substrate. Thus, the carbon nanotube film structure can be sandwiched between the protein layer and the lyophobic substrate and need not be in contact with the nerve network directly. The carbon nanotube film structure is a lyophobic article and is not capable of defining a hydrophilic and bio-compatible surrounding to form the nerve network thereon or acting as a biological substrate. Thus, as long as the protein layer is located on the carbon nanotube film structure to form the culture layer, the nerve network can be located on the carbon nanotube film structure.

In one embodiment, the culture layer is fabricated by the following steps:

S11, providing the lyophobic substrate;

S12, placing the carbon nanotube film structure on a surface of the lyophobic substrate; and S13, soaking the carbon nanotube film structure located on the lyophobic substrate with a protein solution to form the protein layer.

In step S12, the carbon nanotube film structure can cover the surface of the lyophobic substrate or be located on part of the surface of the lyophobic substrate. To decrease a specific surface area of the carbon nanotube film structure and increase an adhesive attraction force between the carbon nanotube film structure and the lyophobic substrate, the step S12 can further include the following steps: S121, soaking the carbon nanotube film structure located on the surface of the lyophobic substrate with an organic solvent; and S122, evaporating the organic solvent out of the carbon nanotube film structure.

In step S13, means for soaking the carbon nanotube film structure with the protein solution is not limited, provided the protein of the protein solution can be adhered to the surface of the carbon nanotube structure to form the protein layer. For example, the protein solution can be sprayed on the surface of the carbon nanotube film structure to soak the carbon nanotube film structure with the protein solution. In one embodiment, to soak the carbon nanotube film structure with the protein solution, the step S13 includes a step of dipping the carbon nanotube film structure located on the lyophobic substrate into the protein solution. A dipping time is not limited, provided most of the carbon nanotubes of the carbon nanotube film structure are soaked with the protein solution and the protein does not deteriorate. In one embodiment, the carbon nanotube film structure is dipped in a cow's blood serum for about 1.5 hours.

When the carbon nanotube film structure is dipped in the protein solution, part of the carbon nanotubes or all of the carbon nanotubes can be soaked by the protein solution. Generally, the greater the dipping time, the more the carbon nanotubes of the carbon nanotube film structure can be soaked by the protein solution. The smaller a thickness of the carbon nanotube film structure, the more the carbon nanotubes of the carbon nanotube film structure can be soaked by the protein solution.

The step S10 can further include a step of S14, sterilizing the protein layer. Means for sterilizing the protein layer is not limited, provided nearly all of the bacteria distributed in the protein layer can be killed. The protein layer can be sterilized by means of an ultraviolet sterilization technology or a high temperature sterilization technology. If the protein layer is sterilized by means of high temperature sterilization technology, a temperature of the protein layer should be less than about 220 degrees, thus the protein layer cannot be damaged. In one embodiment, the temperature of the protein layer is about 120 degrees. A rigidity of the protein layer can be increased if the protein layer is sterilized because part of the water in the protein layer can be evaporated.

The step S10 can further include a step of S15: introducing a poly-D-lysine (PDL) layer on a surface of the protein layer away from the lyophobic substrate. In the step S15, the poly-D-lysine layer can increase an adhesive attraction force between the culture layer and the nerve cells by forming a plurality of changes on the surface of the culture layer. The poly-D-lysine layer can be formed by dipping the protein layer located on the lyophobic substrate into a poly-D-lysine solution. A concentration of the poly-D-lysine in the poly-D-lysine solution can be about 20 milligrams per milliliter.

In the step S20, the nerve cells can be from a mammal, such as human, a mouse, or a cow. The nerve cells are neurons. In one embodiment, the nerve cells are hippocampal neurons from a mouse. The nerve cells can be seeded on the protein layer by spraying a nerve cells solution to the surface of the protein layer, or by dipping the culture layer into the nerve cells solution. If the culture layer is dipped into the nerve cells solution, the nerve cells solution can be received in a culture dish and the protein layer is not in contact with the culture dish. In one embodiment, a surface of the lyophobic substrate away from the protein layer is in contact with the culture dish, to separate the protein layer and the culture dish. When the protein layer is covered by the cells solution, the nerve cells in the nerve cells solution can be deposited or seeded on the surface of the protein layer.

In step S30, surrounding conditions for culturing the nerve cells are not limited, provided the neurites can branch from the nerve cells and be connected between the nerve cells. The nerve cells can be cultured under a room temperature and an ordinary pressure. The nerve cells can also be cultured under a condition similar to a condition in a mammal. Cell growth factors can be provided by the protein layer to culture the nerve cells. Alternatively, the lyophobic substrate cannot define the growth surrounding for the nerve cells, thus, the nerve cells can only be cultured on the surface of the carbon nanotube film structure with the protein layer thereon. The nerve network can only be located on the carbon nanotube film structure with the protein layer thereon and combined with the carbon nanotube film structure.

The neurites can include dendrites or axons. Generally, the neurites can grow in all directions from one nerve cell. But if there are a plurality of nerve cells located on the surface of the protein layer, the neurites from one nerve cell would preferentially extend to adjacent nerve cells. Thus, growth directions of the neurites can be guided by positions of the nerve cells.

In the method for making the nerve graft, the carbon nanotube film structure can be sandwiched between the lyophobic substrate and the protein layer to form the culture layer. The culture layer can define a grow surrounding, thus the nerve network can be formed on the culture layer. All of the lyophobic substrate, the protein layer and the carbon nanotube film can have a good tactility, nonmetal and biocompatible properties, thus the culture layer including the lyophobic substrate, the protein layer and the carbon nanotube film structure can be transplanted into a biological body and form a shape as desired. Therefore, the shape and a thickness of the culture layer can be designed as a shape and a thickness of a wound of the biological body, such as a human wound. The nerve cells of the nerve network can communicate with each other, thus if the nerve graft is transplanted into the wound, nerve cells of the biological body close to the wound and the nerve network can be connected together. An area of the wound can be substantially equal to an area of the nerve graft, and a distance between an edge of the nerve graft and an edge of the wound can be less than a length of the wound. Therefore, a distance between the nerve cells of the biological body close to the wound and the nerve network can be less than the length of the wound. The less the distance between the nerve cells of the biological body close to the wound and the nerve network, the less the time of connecting the nerve network and the nerve cells of the biological body, the less the time recovering the wound.

In addition, generally, the carbon nanotubes are pure carbon nanotubes consisting primarily of carbon atoms. The carbon nanotubes can also include carbon nanotubes that are modified, to form a plurality of functional groups, such as hydrophilic functional groups. But the functional groups do not contribute to the method for making the nerve graft, because the functional groups are substantially covered or wrapped by the protein layer.

Figure 5:
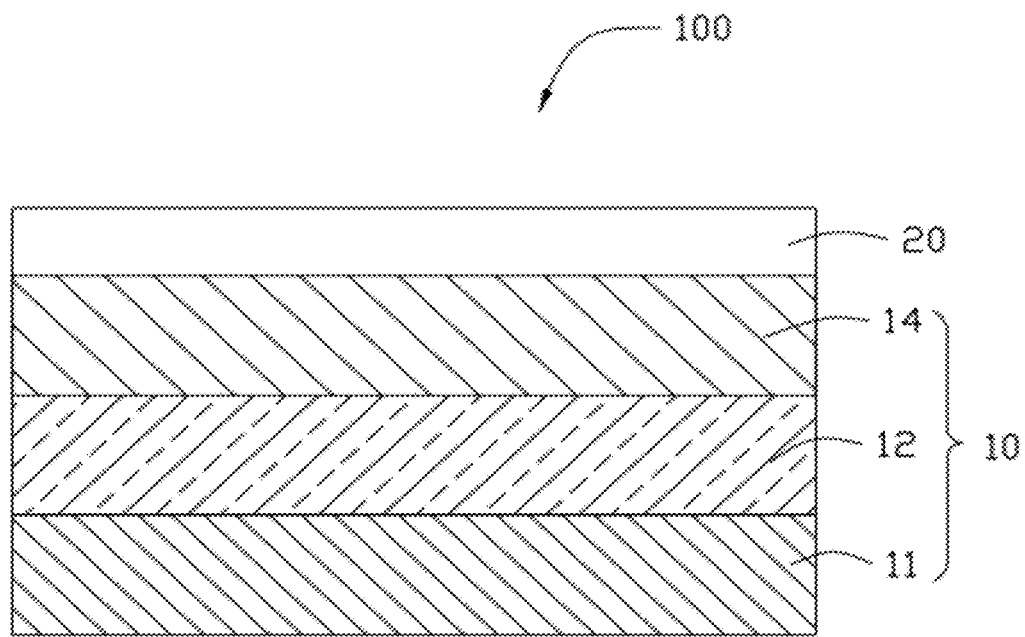
FIG. 5 shows a side view of the nerve graft.
Figure 6:
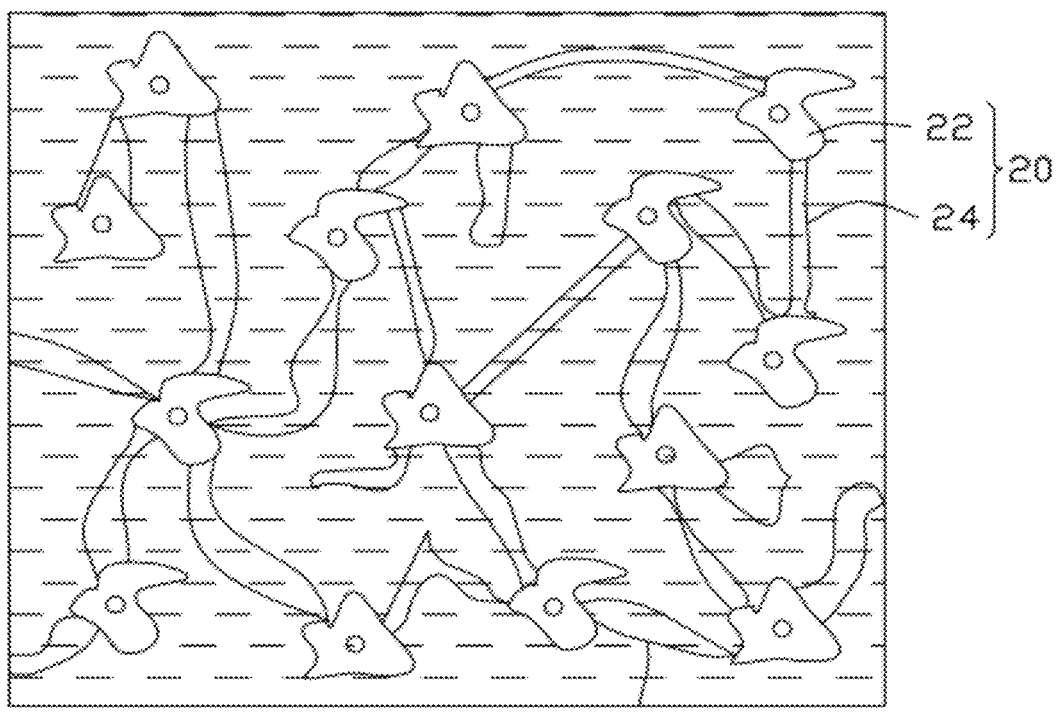
FIG. 6 shows a top view of the nerve graft.

The nerve graft of one embodiment can be fabricated by the method mentioned above. Referring to FIG. 5, the nerve graft 100 can include a culture layer 10 and a nerve network 20 located on a surface of the culture layer 10.

The culture layer 10 includes a lyophobic substrate 11, a carbon nanotube film structure 12, and a protein layer 14. The carbon nanotube film structure 12 is sandwiched between the lyophobic substrate 11 and the protein layer 14. The carbon nanotube film structure 12 can be disposed on one surface of the lyophobic substrate 11, or on two opposite surfaces of the lyophobic substrate 11. In one embodiment, the culture layer 10 only includes one carbon nanotube film structure 12 disposed on one surface of the lyophobic substrate 11.

The lyophobic substrate 11 is configured to load the carbon nanotube film structure 12. The lyophobic substrate 11 can improve a mechanical strength of the culture layer 10, and prevent the carbon nanotube film structure 12 from being damaged by an external force. The lyophobic substrate 11 has a lyophobic property, thus a biological element such as the nerve cell, cannot be cultured in a growth surrounding defined by the lyophobic substrate 11. The lyophobic substrate 11 is innoxious to the biological element, such as the nerve cell, thus the lyophobic substrate 11 is suitable for being transplanted into a biological body. In one embodiment, the lyophobic substrate 11 is a silica gel substrate or a substrate coated with silica gel. The lyophobic substrate 11 can also be a soft substrate. As such, a shape or an area of the lyophobic substrate 11 can be formed as desired.

Macroscopically, the carbon nanotube film structure 12 is a planar structure and capable of forming a free-standing structure. The carbon nanotube film structure 12 includes a plurality of carbon nanotubes substantially parallel to a surface of the corresponding carbon nanotube film structure 12. The carbon nanotube film structure 12 can include at least one carbon nanotube film. If the carbon nanotube film structure 12 includes a plurality of carbon nanotube films, the carbon nanotube films can be stacked together, and adjacent carbon nanotube films can be adhered by only van der Waals attractive force therebetween. The carbon nanotube film can be a flocculated carbon nanotube film as shown in FIG. 2, a pressed carbon nanotube film as shown in FIG. 3, and a drawn carbon nanotube film as shown in FIG. 4. In one embodiment, the carbon nanotube film structure 12 includes a plurality of drawn carbon nanotube films stacked together. Aligned directions of adjacent drawn carbon nanotube films are substantially perpendicular to each other. A thickness of the carbon nanotube film structure 12 is not limited. Generally, the thickness of the carbon nanotube film structure 12 can be from about 0.3 micrometers to about 60 micrometers. In one embodiment, the thickness of the carbon nanotube film structure 12 is about 0.6 micrometers.

The protein layer 14 can include fibrous protein, enzyme protein, or blood serum. The protein layer 14 can include soluble protein and insoluble protein. The term "soluble protein" can be defined as a protein capable of interacting with water. There can be a plurality of hydrophilic amino acids disposed on the outer surface of the soluble protein. In one embodiment, the protein layer 14 includes blood serum of a mammal, such as a cow, a pig, or human. The blood serum cannot only be capable of defining a hydrophilic and biocompatible surrounding on the carbon nanotube film structure 12, but also capable of supplying a cell growth factor for the nerve cells or the nerve network 20.

A thickness of the protein layer 14 is not limited, provided the hydrophilic and biocompatible surrounding can be defined on the carbon nanotube film structure 12. The thickness of the protein layer 14 can be from about 0.3 micrometers to about 2 micrometers. In one embodiment, the thickness of the protein layer 14 is about 0.6 micrometers. Macroscopically, the protein layer 14 is located on a surface of the carbon nanotube film structure 12 away from the lyophobic substrate 11. Microscopically, the protein layer 14 can penetrate into the carbon nanotube film structure 12 and wrap part of or all of the carbon nanotubes of the carbon nanotube film structure 12. Therefore, an obvious interface cannot be defined between the carbon nanotube film structure 12 and the protein layer 14. The less the thickness of the carbon nanotube film structure 12, the more the carbon nanotube film structure 12 can be wrapped by the protein layer 14.

The nerve network 20 is disposed on a surface of the protein layer 14 away from the lyophobic substrate 11. The neurites 24 can be dendrites or axons. The nerve network 20 includes a plurality of nerve cells 22 and a plurality of neurites 24 branching from the nerve cells 22 and connected among the nerve cells 22. The number of the neurites 24 branching from each of the nerve cells 22 is not limited, provided at least two nerve cells 22 are connected by at least one neurite 24. Each of the neurites 22 can be connected between two neurites 24, or be connected to only one neurite 24, provided at least two nerve cells 22 are connected by at least one neurite 24.

The culture layer 10 combining with the nerve network 20 can have good tactility, nonmetal and biocompatible properties, thus the culture layer 10 can be transplanted into a biological body, such as human. Thus, a shape and a thickness of the nerve graft 100 can be designed as a shape and a thickness of a wound of the biological body. The nerve cells 22 of the nerve network 20 can communicate with each other by the neurites 24, thus if the nerve graft 100 is transplanted into the wound, nerve cells 22 of the biological body close to the wound and the nerve network 20 can be connected together. An area of the wound can be substantially equal to an area of the nerve graft 100, and a distance between an edge of the nerve graft 100 and an edge of the wound can be less than the length of the wound. Therefore, a distance between the nerve cells 22 of the biological body close to the wound and the nerve network 20 can be less than the length of the wound. The less the distance between the nerve cells 22 of the biological body close to the wound and the nerve network 20, the less time it takes to connect the nerve network 20 and the nerve cells 22 of the biological body with the neurites 24, and the less the time it takes for the wound to heal.

A method for making a nerve graft of one detailed embodiment can include the following steps:

S210, providing a silica gel substrate;

S220, placing a carbon nanotube film structure on a surface of the silica gel substrate;

S230, dipping the silica gel substrate with the carbon nanotube film structure placed thereon into a cow's blood serum to soak the carbon nanotube film structure with the cow's blood serum, thus allowing a cow's blood serum layer to form the carbon nanotube film structure;

S240, taking the silica gel substrate with the carbon nanotube film structure and the cow's blood serum layer placed thereon out of the cow's blood serum solution, and sterilizing the cow's blood serum layer under a temperature of about 120 degrees;

S250, dipping the sterilized cow's blood serum layer into a poly-D-lysine solution to form a poly-D-lysine layer on the cow's blood serum layer, and thus a culture layer including the silica gel substrate, the carbon nanotube film structure, the protein layer, and the poly-D-lysine layer is formed;

S260, covering the culture layer with a nerve cell solution until a plurality of nerve cells 22 dissolved in the nerve cell solution are deposited on a surface of the poly-D-lysine layer away from the lyophobic substrate; and S270, culturing the plurality of nerve cells 22 until a plurality of neurites 24 branch from the nerve cells 22 and are connected among the plurality of nerve cells 22.

In step S210, the silica gel substrate includes silica gel. The silica gel is innoxious to the biological element, such as the nerve cell. Thus, the silica gel substrate can be suitable for loading the nerve network and transplanted into a biological body to recover a nervous system. The silica gel substrate is also a soft substrate. A shape or an area of the silica gel substrate can be formed as desired. The shape of the silica gel substrate can correspond to a shape of a wound of the nervous system, and the area of the silica gel substrate can correspond to an area of the wound of the nervous system.

Figure 7:
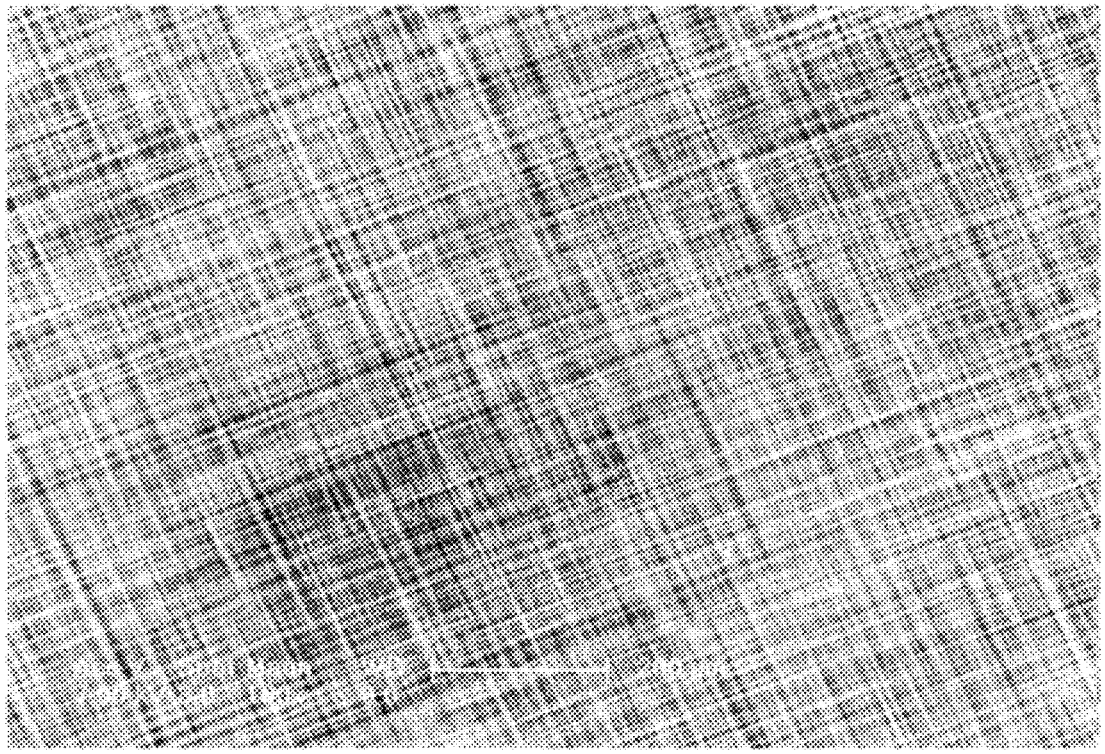
FIG. 7 shows an SEM image of a carbon nanotube film structure consisting of a plurality of stacked drawn carbon nanotube films.
Figure 8:
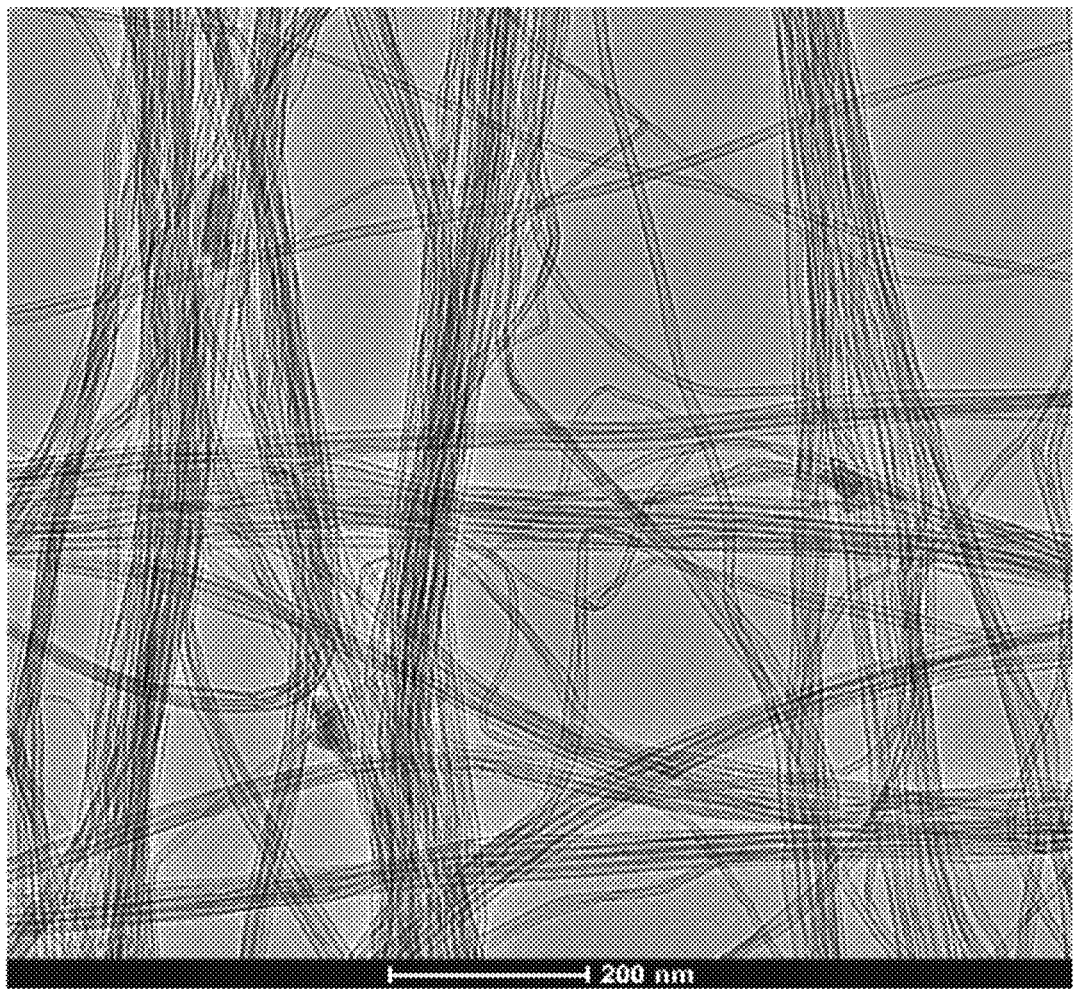
FIG. 8 shows a Transmission Electron Microscope (TEM) image of the carbon nanotube film structure.

In step S220, to decrease a specific surface area of the carbon nanotube film structure and increase an adhesive attraction force between the carbon nanotube film structure and the silica gel substrate, the step S220 can further include the following steps: S221, soaking the carbon nanotube film structure located on the surface of the lyophobic substrate with an organic solvent; and S222, evaporating the organic solvent out of the carbon nanotube film structure. Referring to FIG. 7 and FIG. 8, the carbon nanotube film structure includes a plurality of drawn carbon nanotube films stacked together; aligned directions of adjacent drawn carbon nanotube films are substantially perpendicular to each other.

Figure 9:
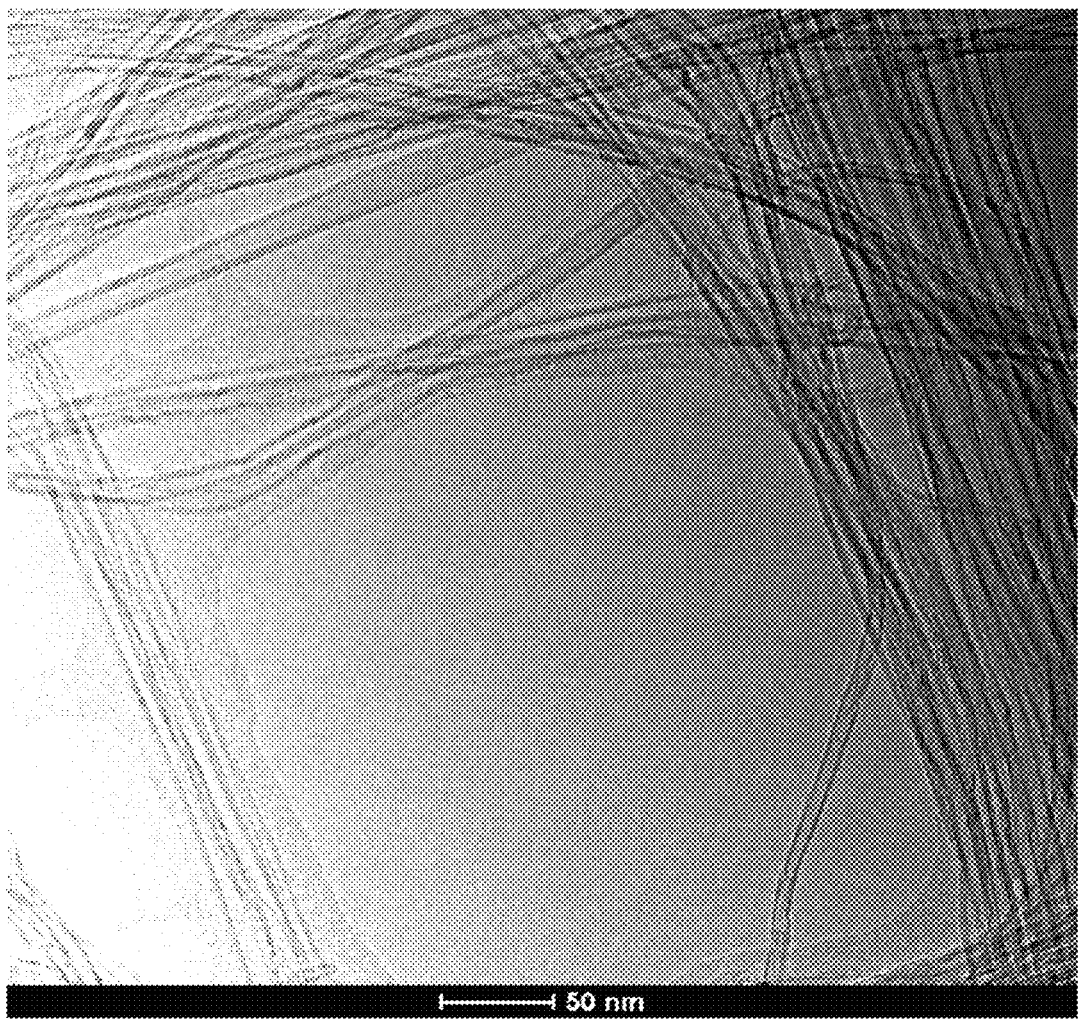
FIG. 9 shows a TEM image of a culture layer.

In step S230, the cow's blood serum is pure liquid cow's blood serum. When the carbon nanotube film structure is dipped into the cow's blood serum, the carbon nanotube film structure is difficult to be damaged by a surface tension of the cow's blood serum because of the support of the silica gel substrate. A dipping time for dipping the carbon nanotube film structure can be determined by a thickness of the carbon nanotube film structure. The less the thickness of the carbon nanotube film structure, the shorter the dipping time. In one embodiment, the thickness of the carbon nanotube film structure is about 0.6 micrometers, and the dipping time is about 1.5 hours. If the carbon nanotube film structure has a thickness of about 0.6 micrometers dipped in the cow's blood serum for about 1.5 hours, the cow's blood serum layer can be formed on the carbon nanotube film structure as shown in FIG. 9.

A rigidity of the protein layer can be increased if the protein layer is sterilized under the temperature, because part of the water in the protein layer can be evaporated.

In the step S250, the poly-D-lysine layer is disposed on a surface of the cow's blood serum layer away from the lyophobic substrate. The poly-D-lysine layer can increase an adhesive attraction force between the culture layer and the nerve cells by forming a plurality of changes on the surface of the culture layer. A concentration of the poly-D-lysine in the poly-D-lysine solution can be about 20 milligrams per milliliter.

In the step S260, the nerve cells 22 can be from a mammal, such as a human, a mouse, or a cow. The nerve cells 22 are neurons. In one embodiment, the nerve cells 22 are hippocampal neurons from a mouse. If the culture layer is dipped into the nerve cells solution, the nerve cells solution can be received in a culture dish and the cow's blood serum layer is not in contact with the culture dish. In one embodiment, a surface of the lyophobic substrate away from the cow's blood serum layer is in contact with the culture dish to separate the cow's blood serum layer and the culture dish. When the cow's blood serum layer is covered by the cells solution, the nerve cells in the nerve cells solution can be deposited or seeded on the surface of the cow's blood serum layer.

Figure 10:
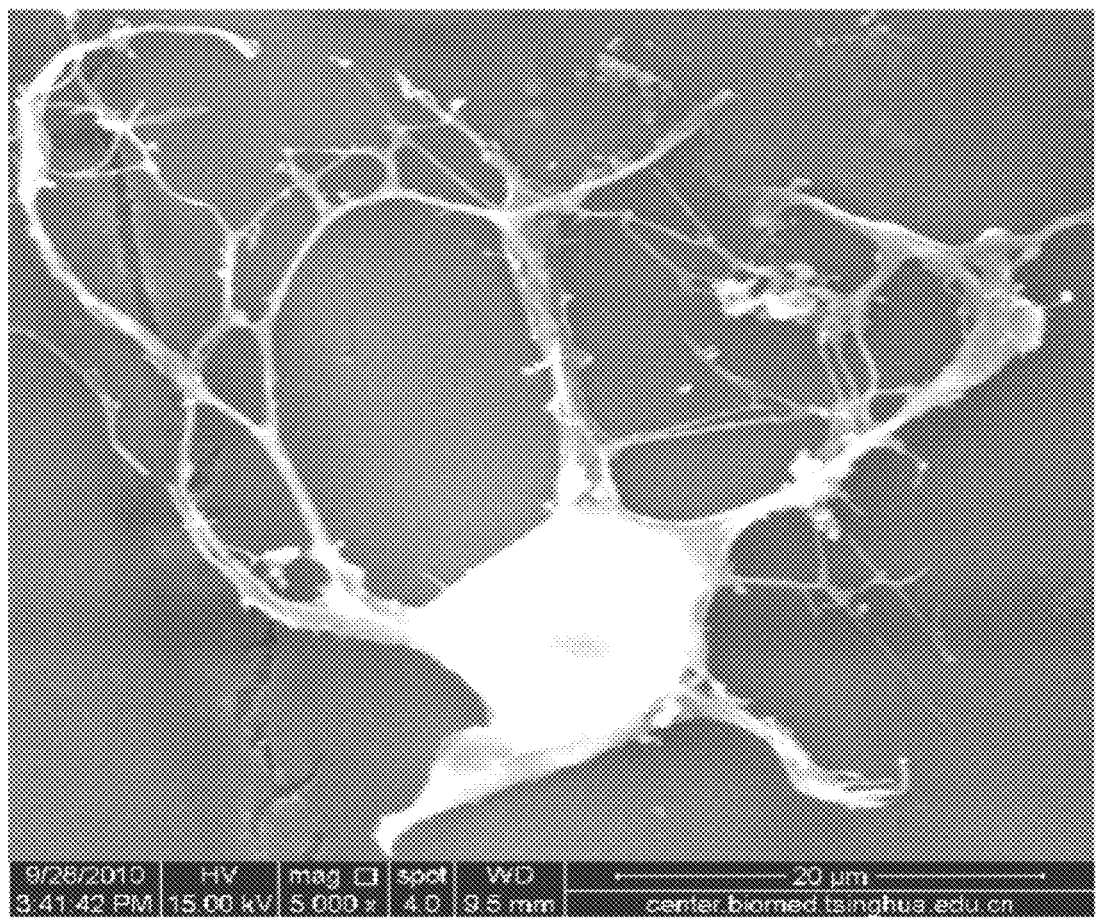
FIG. 10 shows an SEM image of one nerve cell cultured on the culture layer.

In step S270, surrounding conditions for culturing the nerve cells 22 are not limited, provided the neurites 24 can branch from the nerve cells 22 and be connected between the nerve cells. The nerve cells 22 can also be cultured under room temperature and an atmospheric pressure. The nerve cells can be cultured under a condition similar to a condition in a mammal Referring to FIG. 10, when one of the nerve cells 22 seeded on the culture layer are cultured in a typical room condition for about 15 days, a plurality of neurites 24 branch from one of the nerve cells.

Figure 11:
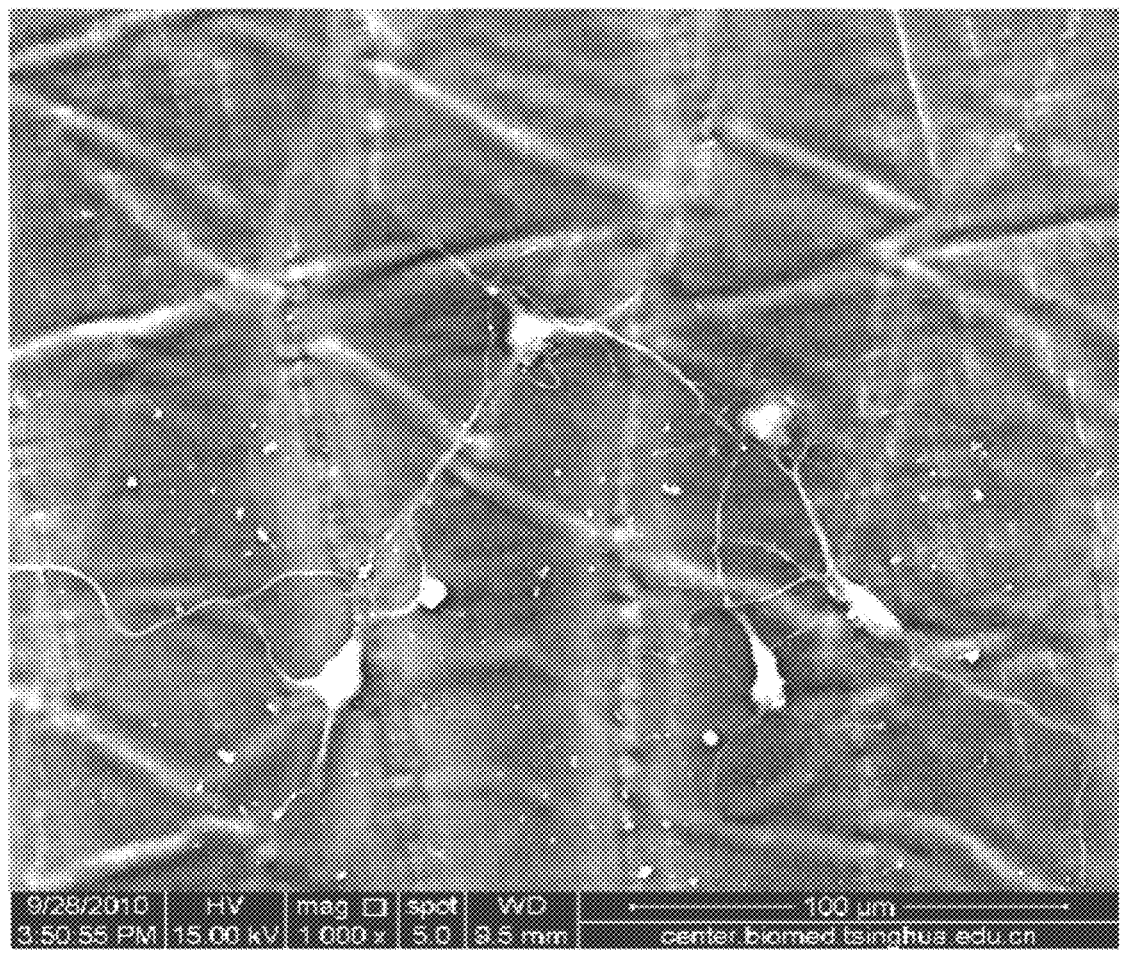
FIG. 11 shows an SEM image of a nerve graft, wherein a nerve network of the nerve graft are dyed.
Figure 12:
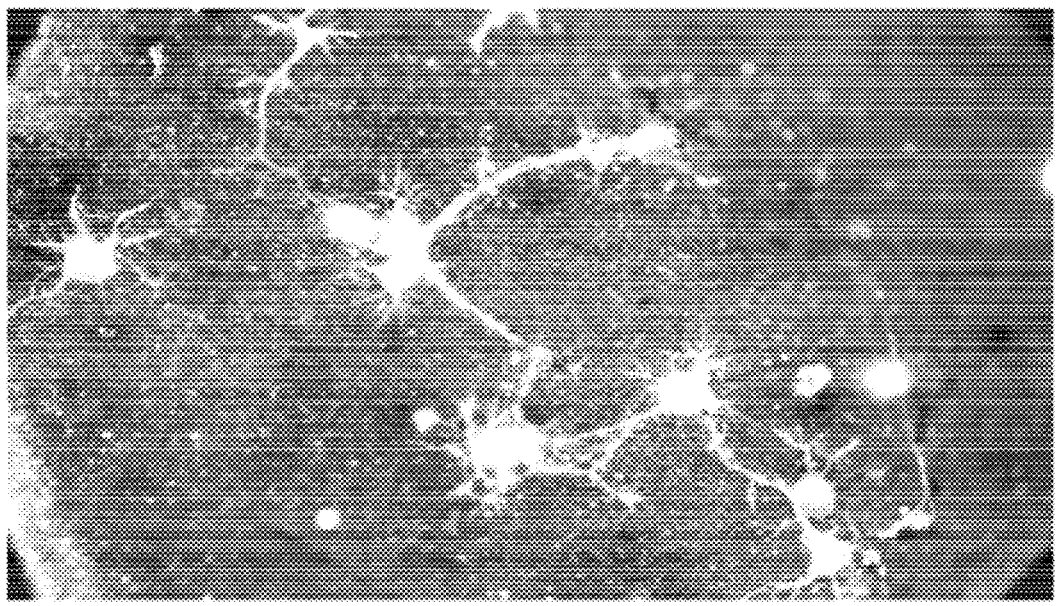
FIG. 12 shows an SEM image of the nerve graft, wherein the nerve network of the nerve graft are not dyed.

The neurites 24 can be dendrites or axons. Generally, the neurites 24 can grow in all directions from one nerve cell. Referring to FIG. 11 and FIG. 12, if there are a plurality of nerve cells located one the surface of the cow's blood serum layer, the neurites from one nerve cell would preferentially extend to adjacent nerve cells. Thus, growth directions of the neurites can be guided by positions of the nerve cells. The nerve cells can also be connected by the neurtites to form the nerve network. Cell growth factors can be provided by the cow's blood serum layer for culturing the nerve cells. Alternatively, the lyophobic substrate cannot define the growth surrounding for the nerve cells, the nerve cells can only be cultured on the surface of the carbon nanotube layer with cow's blood serum layer thereon. The nerve network can only be located on the carbon nanotube layer with cow's blood serum layer thereon and combined with the carbon nanotube layer.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure.

The above-described embodiments illustrate the scope of the disclosure but do not restrict the scope of the disclosure.

What is claimed is:

1. A method for making a nerve graft, comprising:
   fabricating a culture layer comprising a lyophobic substrate, a protein layer, and a carbon nanotube film structure sandwiched between the lyophobic substrate and the protein layer to form a three-layer structure, the carbon nanotube film structure being a free-standing structure and comprising a plurality of drawn carbon nanotube films stacked with each other, wherein adjacent carbon nanotube films are combined and attracted to each other by van der Waals attractive force therebetween, each of the plurality of carbon nanotube films comprises a plurality of carbon nanotubes oriented along a direction that is substantially parallel to a surface of the carbon nanotube film structure, and joined end to end along the same direction by van der Waals force, an angle between two orienting directions of carbon nanotubes of the adjacent carbon nanotube films is about 90 degrees, and the lyophobic substrate is a silica gel substrate or a substrate coated with silica gel;
   seeding a plurality of nerve cells on a surface of the protein layer spaced away from the lyophobic substrate; and
   culturing the purality of nervecells untila plurality of neurites are branched from the plurality of nerve cells and connected between the plurality of nerve cells to form a nerve network;
   wherein the fabricating the culture layer comprises the steps of:
   providing the lyophobic substrate,
   placing the carbon nanotube film structure on a surface of the lyophobic substrate, and
   soaking the carbon nanotube film structure located on the lyophobic substrate with a protein solution to form the protein layer that has a thickness in the range of from about 0.3 micrometers to about 2 micrometers.

2. The method of claim 1, wherein each of the plurality of nerve cells is connected to one adjacent nerve cell of the plurality of nerve cells by at least one of the plurality of neurites.

3. The method of claim 1, wherein the plurality of neurites comprise dendrites and axons.

4. The method of claim 1, wherein the protein layer comprises soluble protein.

5. The method of claim 4, wherein the protein layer comprises blood serum of a mammal.

6. The method of claim 1, wherein the placing the carbon nanotube film structure on the surface of the lyophobic substrate comprises:
   soaking the carbon nanotube film structure located on the lyophobic substrate with an organic solvent; and
   evaporating the organic solvent out of the carbon nanotube film structure.

7. The method of claim 1, wherein the soaking the carbon nanotube film structure located on the lyophobic substrate with the protein solution comprises dipping the carbon nanotube film structure located on the lyophobic substrate into the protein solution.

8. The method of claim 1, wherein the soaking the carbon nanotube film structure located on the lyophobic substrate with the protein solution comprises spraying the protein solution on a surface of the carbon nanotube film structure.

9. The method of claim 1, wherein the fabricating the culture layer further comprises introducing a poly-D-lysine layer on a surface of the protein layer spaced away from the lyophobic substrate.

10. The method of claim 1, wherein the fabricating the culture layer further comprises sterilizing the protein layer.

11. The method of claim 10, wherein the protein layer is sterilized by means of an ultraviolet sterilization technology, a high temperature sterilization technology, or a refrigeration sterilization technology.

12. The method of claim 1, wherein the plurality of neurites are oriented along the same orientation.

* * * * *